(12) United States Patent
Magee et al.

(10) Patent No.: US 6,648,866 B2
(45) Date of Patent: Nov. 18, 2003

(54) ABSORBENT ARTICLE FASTENING DEVICE

(75) Inventors: Luke Robinson Magee, Cincinnati, OH (US); Mark Mason Hargett, Cincinnati, OH (US); Mark James Kline, Okeana, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/994,191

(22) Filed: Nov. 26, 2001

(65) Prior Publication Data

US 2003/0100880 A1 May 29, 2003

(51) Int. Cl.⁷ ................................................ A61F 13/15
(52) U.S. Cl. .................. 604/385.03; 604/389; 604/391
(58) Field of Search .............................. 604/386, 387, 604/389, 390, 391, 385.03, 385.05

(56) References Cited

U.S. PATENT DOCUMENTS

| | | | |
|---|---|---|---|
| 3,869,761 A | * | 3/1975 | Schaar ........................ 24/304 |
| 3,926,191 A | * | 12/1975 | Tritsch ....................... 604/390 |
| 4,643,730 A | * | 2/1987 | Chen et al. ................. 604/390 |
| 4,963,140 A | | 10/1990 | Robertson et al. |
| 5,019,065 A | | 5/1991 | Scripps |
| 5,053,028 A | | 10/1991 | Zoia et al. |
| 5,108,384 A | | 4/1992 | Goulait |
| 5,599,601 A | | 2/1997 | Polski et al. |
| 5,605,735 A | * | 2/1997 | Zehner et al. ............... 428/100 |
| 5,611,789 A | | 3/1997 | Seth |
| 5,624,428 A | | 4/1997 | Sauer |
| 5,725,714 A | * | 3/1998 | Fujioka et al. .............. 156/259 |
| 5,899,895 A | * | 5/1999 | Robles et al. .......... 604/385.29 |
| 5,926,926 A | | 7/1999 | Kato |
| 6,045,543 A | * | 4/2000 | Pozniak et al. ......... 604/385.01 |
| 6,063,466 A | | 5/2000 | Tuschy et al. |
| 6,142,986 A | | 11/2000 | Lord et al. |
| 6,174,303 B1 | | 1/2001 | Suprise et al. |
| 6,251,097 B1 | * | 6/2001 | Kline et al. ................. 604/387 |

FOREIGN PATENT DOCUMENTS

| | | |
|---|---|---|
| EP | 0 756 855 B1 | 11/2000 |
| EP | 0 765 141 B1 | 11/2000 |
| WO | WO 01/43682 A1 | 6/2001 |
| WO | WO 01/43683 A1 | 6/2001 |

* cited by examiner

*Primary Examiner*—Weilun Lo
*Assistant Examiner*—Michael G Bogart
(74) *Attorney, Agent, or Firm*—Jack L. Oney, Jr.; Jeffrey R. Moore; Ken K. Patel

(57) ABSTRACT

A dual fastening device suitable for pull-up and cinch use with absorbent articles. The fastening device preferably includes a first fastening member and a second member.

17 Claims, 5 Drawing Sheets

ABSORBENT ARTICLE FASTENING DEVICE

FIELD OF THE INVENTION

The present invention relates to an improved fastening device for absorbent articles such as diapers, training pants, and pull-ups. More particularly, the present invention relates to improved fasteners for joining the front of a disposable absorbent article to the rear of the article with an improved combination of application ease and fit.

BACKGROUND OF THE INVENTION

Conventional absorbent articles, such as disposable diapers and training pants have typically employed adhesive or mechanical fasteners which attach appointed waistband sections of the articles around a wearer's waist. In addition, various configurations of waist elastics, leg elastics, and elasticized outercovers have been used on absorbent articles to help produce and maintain the article about the body contours of the wearer.

Conventional absorbent articles, such as those described above, have not provided desired levels of reliable fit, and have been susceptible to excessive sagging and drooping during wearing. The articles have not adequately maintained the desired levels of fit, comfort and ease of use. Where the garment has been constructed with more aggressive fasteners to better maintain the desired fit, undesirable skin marking and/or a difficult to remove article may result. As a result, there has been a continued need for garments having more consistent fit, greater resistance to sagging and drooping, and greater ease in the application and removal of the article. Accordingly, it is an object of the present invention to provide an improved article fastening device.

SUMMARY OF THE INVENTION

An absorbent article having a first waist region, a second waist region and a crotch region. The crotch region interconnects the first waist region and second waist region. The absorbent article includes an article inner surface, an article outer surface a topsheet, a backsheet, and an absorbent core interposed between the topsheet and the backsheet and a fastening device. The fastening device joins at least a portion of the first waist region with at least a portion of the second waist region. The fastening device includes at least one first fastening member, and at least one second fastening member. The first fastening member is joined to the first waist region. The first fastening member includes at least one first tab. The first tab includes a first tab inner surface, a first tab outer surface, and a first tab fastening element on the first tab inner surface, and at least one second tab. The second tab includes a second tab inner surface, a second tab outer surface, and a second tab fastening element on the second tab inner surface. The fastening device is designed to allow an article user to hold one element of the fastening device such as the first tab, and connect the first and second waist regions in at least two places. This is achieved through manipulation of bond strengths between the fastening device elements. The fastening device includes means for providing a releasable combined tab fastening bond strength between the first tab outer surface and the second tab inner surface. A second fastening member is joined to the second waist region on the article outer surface and includes at least one attachment landing zone. Each first tab fastening element and second tab fastening element are configured to provide an operably secure, fastening engagement with the attachment landing zone. The fastening device may include at least one stored landing zone on the article inner surface and means for providing a releasable storage fastening bond strength between the stored landing zone and the first fastening member. The releasable storage fastening bond strength may be less than the releasable combined tab fastening bond strength. The fastening device may include a means for providing a first releasable fastening bond strength between the first tab fastening element and the attachment landing zone that is stronger than the means for providing the releasable combined tab fastening bond strength. A means for providing a second releasable fastening bond strength between the second tab fastening element and the attachment landing zone may be greater than or equal to the means for providing the first releasable fastening bond strength.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like numerical designations are used to designate substantially identical elements, and in which:

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and studying the included drawings.

Figure 1:
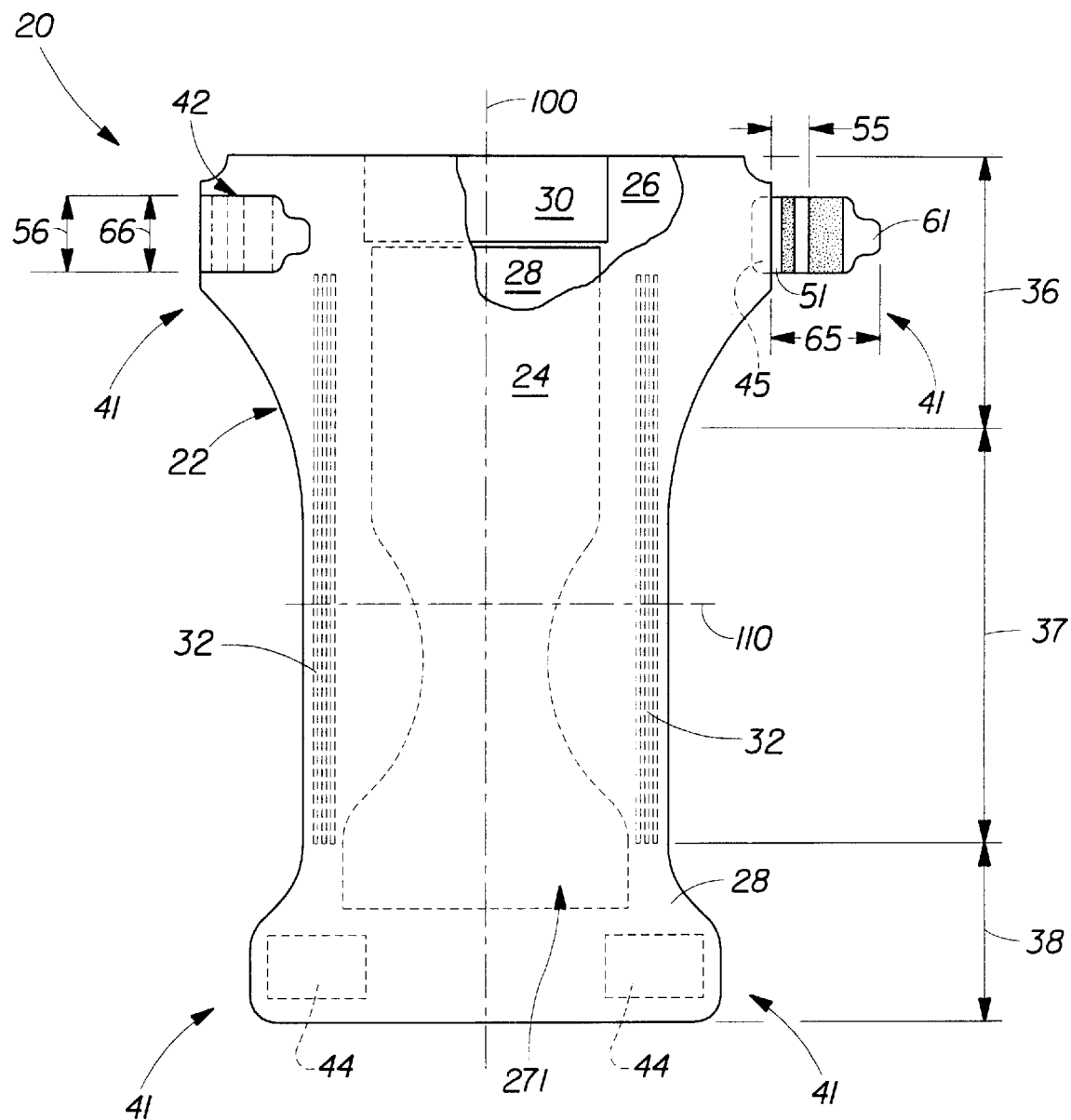
FIG. 1 is a plan view of one embodiment of an absorbent article in its flat out uncontracted state with the body-facing surface of the absorbent article facing the viewer.

The present invention provides a pull-up and cinch dual fastener fastening system. Various aspects of the invention are herein described in terms of an absorbent article such as a diaper 20 as shown in FIG. 1. However, it is readily apparent that the present invention may also be used to fasten other wearable articles such as disposable absorbent training pants, incontinence briefs, incontinence undergarments, and any other article wherein a fastening device with the characteristics herein disclosed is desired.

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Disposed" is used to mean that an element(s) is formed (joined and positioned) in a particular place or position as a unitary structure with other elements or as a separate element joined to another element.

A "unitary" absorbent article refers to absorbent articles which are formed of separate parts united together to form a coordinated entity so that they do not require separate manipulative parts like a separate holder and liner.

"Diaper" refers to an absorbent article generally worn by infants and incontinent persons about the lower torso.

"Impermeable" generally refers to articles and/or elements that are not penetrative by fluid through the entire z-directional thickness of the article under pressure of 0.14 lb/in$^2$ or less. Preferably, the impermeable article or element is not penetrative by fluid under pressures of 0.5 lb/in$^2$ or less. More preferably, the impermeable article or element is not penetrative by fluid under pressures of 1.0 lb/in$^2$ or less.

"Operatively associated" refers to elements which are directly or indirectly joined together so as to function generally as a single element.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Directly joined" refers to elements which are joined to each other without any intermediate elements joined therebetween, except for the means joining the elements (e.g. the adhesive).

"Indirectly joined" refers to elements joined with each other by means of an element or elements other than the joining means.

"Target circumference" is the circumference of a wearer's waist at the location where the article is designed to be applied about the wearer an secured during use.

"Comprise," "comprising," and "comprises" is an open ended term that specifies the presence of what follows e.g. a component but does not preclude the presents of other features, elements, steps or components known in the art, or disclosed herein.

"Engagement" refers to the process by which two fastening elements are fastened.

"Releasable bond" refers to a potentially temporary connection between two or more article components that may be separated during the use of the article.

"Bond strength" or "release load" refers to the minimum amount of force necessary to separate a releasable bond in a time period and fashion consistent with normal use of the article.

"Fastened" refers to the proper connection or attachment of two fastening elements in a fashion consistent with that expected during normal use of the article.

FIG. 1 is a plan view of fastening device 41 attached to a diaper 20 in its flat out, uncontracted state (i.e., without elastic induced contraction). Portions of the structure are cut away to more clearly show the underlying structure of the diaper 20. The portion of the diaper 20 that contacts a wearer is facing the viewer. The diaper 20 may include a longitudinal axis 100 and a transverse axis 110. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment. The crotch region 37 is that portion of the diaper 20 which, when the diaper 20 is worn, is generally positioned between the wearer's legs.

The chassis 22 of the diaper 20 in FIG. 1 comprises the main body of the diaper 20. The chassis 22 comprises an outer covering including a liquid pervious topsheet 24 and/or a liquid impervious backsheet 26. The chassis may include a portion of an absorbent core 28 encased between the topsheet 24 and the backsheet 26. The chassis may also include most or all of the absorbent core 28 encased between the topsheet 24 and the backsheet 26. For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 entitled "Absorbent Article with Dynamic Elastic Waist Feature Having a Predisposed Resilient Flexural Hinge" issued to Buell on Sep. 9, 1992; and U.S. Pat. No. 5,221,274 entitled "Absorbent Article with Dynamic Elastic Waist Feature Having a Predisposed Resilient Flexural Hinge" issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 in FIG. 1 may be fully or partially elasticized or may be foreshortened to provide a void space between the topsheet 24 and the absorbent core 28. Exemplary structures including elasticized or foreshortened topsheets are described in more detail in U.S. Pat. No. 4,892,536 entitled "Absorbent Article Having Elastic Strands" issued to DesMarais et al. on Jan. 9, 1990; U.S. Pat. No. 4,990,147 entitled "Absorbent Article with Elastic Liner for Waste Material Isolation" issued to Freeland on Feb. 5, 1991; U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993; each of which is herein incorporated by reference.

The absorbent core 28 in FIG. 1 generally is disposed between the topsheet 24 and the backsheet 26. The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; U.S. Pat. No. 5,397,316 entitled "Slitted Absorbent Members For Aqueous Body Fluids Formed Of Expandable Absorbent Materials" issued to LaVon et al. on Mar. 14, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The backsheet 26 in FIG. 1 is generally the portion of the diaper 20 positioned with the absorbent core 28 between the backsheet 26 and the topsheet 24. The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references are herein incorporated by reference.

The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092, which are incorporated by reference herein.

In addition, the present invention may be suitable for other diaper embodiments including those disclosed in U.S. Pat. No. 6,010,491 entitled "Viscous Fluid Bodily Waste Management Article" issued Jan. 4, 2000; U.S. Pat. No. 5,873,870 entitled "Fit And Sustained Fit Of A Diaper Via Chassis And Core Modifications" issued Feb. 23, 1999; U.S. Pat. No. 5,897,545 entitled "Elastomeric Side Panel for Use with Convertible Absorbent Articles" issued Apr. 27, 1999; U.S. Pat. No. 5,904,673 entitled "Absorbent Article With Structural Elastic-Like Film Web Waist Belt" issued May 18, 1999; U.S. Pat. No. 5,931,827 entitled "Disposable Pull On Pant" issued Aug. 3, 1999; U.S. Pat. No. 5,977,430 entitled "Absorbent Article With Macro-Particulate Storage Structure" issued Nov. 2, 1999 and U.S. Pat. No. 6,004,306 entitled "Absorbent Article With Multi-Directional Extensible Side Panels" issued Dec. 21, 1999, the disclosures of which are incorporated herein by reference.

Figure 2:
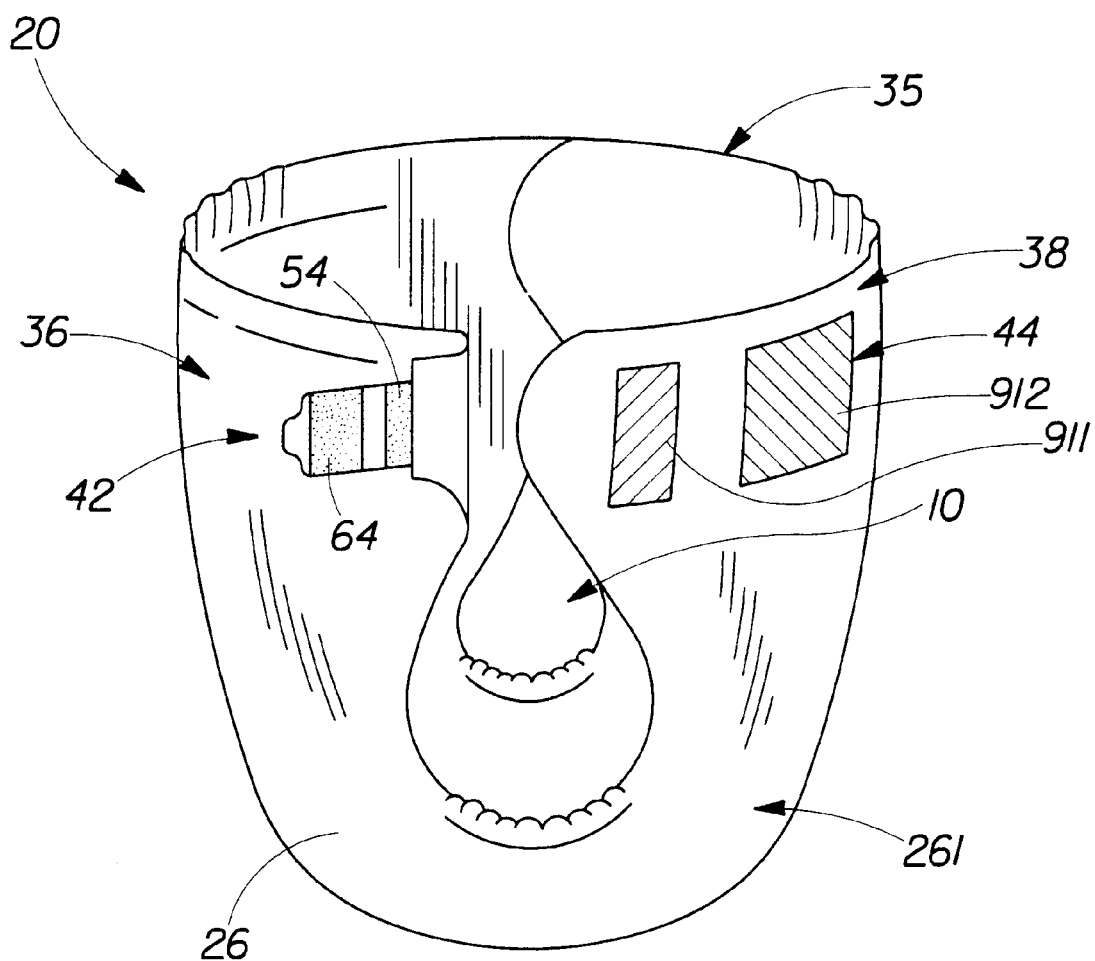
FIG. 2 is a perspective view of one embodiment of the absorbent article.

In order to keep the diaper 20 in place about the wearer, at least a portion of the first waist region 36 is attached by the fastening device 41 to at least a portion of the second waist region 38, preferably to form leg opening(s) 10 and an article waist 35 as shown in FIG. 2. When fastened, the fastening device 41 carries a tensile load around the article waist 35. The fastening device is designed to allow an article user to hold one element of the fastening device such as the first tab, and connect the first waist region 36 to the second waist region 38 in at least two places. This is achieved through manipulation of bond strengths between the fastening device elements.

As shown in FIG. 1, the fastening device 41 may include at least one first fastening member 42, at least one stored landing zone 45, and at least one second fastening member 44. The fastening device 41 and any component thereof may include any material suitable for such a use, including but not limited to plastics, films, foams, nonwoven webs, woven webs, paper, laminates, fiber reinforced plastics and the like, or combinations thereof. It may be preferable that the materials making up the fastening device be flexible. The flexibility is designed to allow the fastening device 41 to conform to the shape of the body and thus, reduces the likelihood that the fastening device 41 will irritate or injure the wearer's skin.

FIG. 2 is a perspective view of the absorbent article 20 as a diaper. The article 20 is presented in a contour similar to that presented when the article 20 is worn. The backsheet 26 forms an article outer surface 261. The first waist region 36 and second waist region 38 generally comprise those portions of the diaper 20 which, when worn about a wearer's waist, encircles the waist of the wearer to form an article waist 35 and leg openings 10. In the foreground, FIG. 2 shows the fastening member 42 separated from the optional stored location and prior to attachment to the second fastening member 44. FIG. 2 also shows the second fastening member 44 comprising two visible components. A first attachment landing zone 911 designed to fasten with the first tab fastening element 54 and a second attachment landing zone 912 designed to fasten with the second tab fastening element 64. Alternatively, the first tab fastening element 54 may be fastened to the second attachment landing zone 912 along with, or in stead of, the second tab fastening element 64.

The first fastening member 42 is designed to be joined to the first waist region 36 as shown in FIG. 1. The first fastening member 42 may be joined, operably connected, or attached to the first waist region 36 in any fashion known in the art. The first fastening member 42 may be of any size and/or shape and may be made from any suitable material. The first fastening member 42 may optionally form an extension from the first waist region 36 in the traverse axis 110 direction. Any portion of the first fastening member 42 may be elastic, inelastic, extensible, or non-extensible. Preferably, the direction of elasticity or extensibility is in the traverse axis 110 directions. The first fastening member 42 may be composed of any suitable materials known in the art. For example, the first fastening member 42 material may be composed of a film or a nonwoven including a spunbonded nonwoven fabric, a spunbond-meltblown-spunbond fabric, a neck-bonded-laminate fabric material, a stretch-bonded-laminate fabric material or the like, as well as combinations thereof as know to those skilled in the art. The first fastening member 42 may include at least one first tab 51 and at least one second tab 61.

The first fastening member 42 is shown on the left side of FIG. 1 in a stored position. The first fastening member 42 is shown on the right side of FIG. 1 is not stored and extended outward in the transverse 110 direction. The first fastening member 42 is preferably stored for shipping and storage. The storage design configuration is designed to decrease storage space requirements and protect the fastening device from inadvertent damage. A first tab width 66 and a second tab width 56 are shown in FIG. 1.

Figure 3:
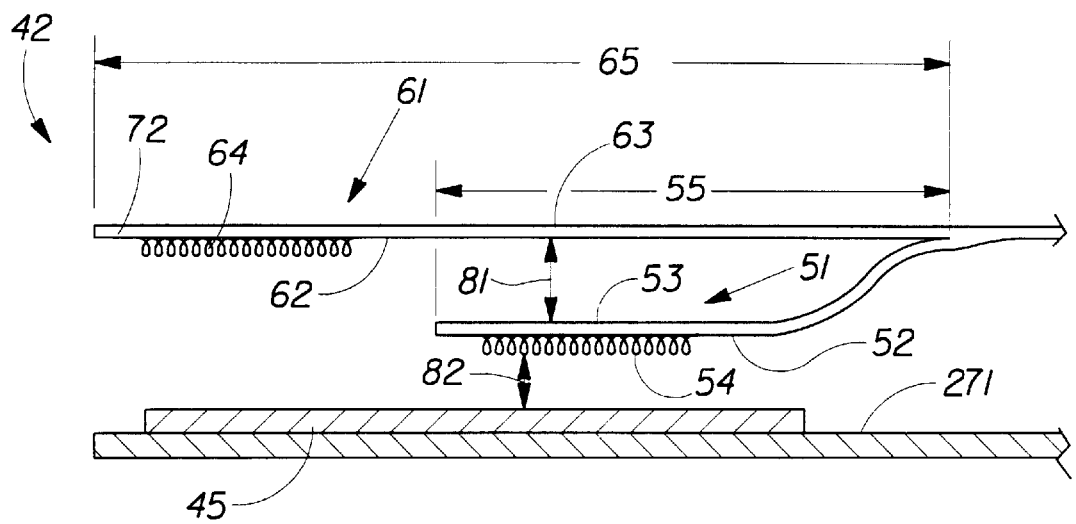
FIG. 3 is an expanded and exploded apart side view of one embodiment of the fastening device and the bonds when stored.

FIG. 3 is an exploded side view of the first fastening member 42 when in a stored condition. The elements of the first fastening member 42 are depicted in FIG. 3 with exaggerated separation to better identify the referenced elements. As shown in FIG. 3, the first tab 51 includes a first tab inner surface 52, a first tab outer surface 53, a first tab fastening element 54, and a first tab length 55. The first tab outer surface 53 is the side opposite the first tab inner surface 52 and is generally the side away from the viewer in FIG. 1. The first tab inner surface 52 corresponds to the surface facing the viewer in FIG. 1 and generally corresponds to the article inner surface 271. A side view of the surfaces is shown in FIG. 3. The first tab fastening element 54 is joined to the first tab inner surface 52 as shown in FIG. 3. The first tab fastening element 54 may include any fastening element known in the art including adhesives, cohesives, hook materials, loop materials, snaps, buttons, tabs, slots, magnets and combinations thereof. The first tab fastening element 54 may have any shape such as a circle, square, rectangle or triangle.

As shown in FIG. 3, the second tab 61 includes a second tab inner surface 62, a second tab outer surface 63, a second tab fastening element 64, and a second tab length 65. The second tab inner surface 62 corresponds to the surface facing the viewer in FIG. 1, a portion of which can be seen in FIG. 1, outward along the traverse axis 110 from the first tab 51. In FIG. 1 and in FIG. 2, the unstored first fastening member 42 has at least a portion of the remaining second tab inner surface 52 disposed under the first tab 51. The second tab outer surface 63 is the side opposite the second tab inner surface 62 and is generally the side away from the viewer in FIG. 1 and is shown in FIG. 3. The second tab fastening element 64 is joined to the second tab inner surface 62 as shown in FIG. 3. The second tab fastening element 64 may include any fastening element known in the art including adhesives, cohesives, hook materials, loop materials, snaps, buttons, tabs, slots, magnets and combinations thereof. The second fastening element 64 may have any shape such as a circle, square, rectangle or triangle.

The first tab 51 and the second tab 61 may be located anywhere in the first waist region 36. The first tab 51 may be preferably located directly under of the second tab 61 such that the first tab outer surface 53 faces the second tab inner surface 62 as shown in FIG. 3. A side view of this arrangement is shown in FIG. 3. The first tab length 55 and the second tab 65 are measured outward along the traverse axis from the same starting point. The starting point may be any location. One starting point may be the traverse outer most point of the backsheet 26 where the tabs begin as shown in FIG. 1. The first tab length 55 may be longer, shorter, or equal to the second tab length 65. Preferably, the first tab length 55 is shorter than the second tab length 65. A shorter first tab length 55 may facilitate manufacturing and/or user manipulation of the first fastening member 42.

As shown in FIG. 1, the fastening device 41 may include at least one stored landing zone 45. The stored landing zone 45 is used to secure the first fastening member 42 in a pre use, stored location. The stored landing zone 45 may be located on the article inner surface 271, or article outer surface 261 (see FIG. 2). Preferably, the stored landing zone 45 is located in the same waist region as the first fastening member 42. Also preferably, the stored landing zone 45 is located on the article inner surface 271 in the first waist region 36 inboard of the first fastening member 42 along the traverse axis 110 as shown in FIG. 1. The stored landing zone 45 may include plastics, adhesives, cohesives, hook materials, loop materials, snaps, buttons, tabs, slots, magnets and combinations thereof as are know to those skilled in the art. The stored landing zone 45 may have any shape such as a circle, square, rectangle or triangle.

FIG. 3 shows the first fastening member 42 in an exploded side view when in a stored, pre-use condition. The exaggerated separation of the elements allows a visual representation of the releasable bonds between the various components. The bonds are designed to be strong enough to function as desired, but weak enough so that a user may break them and separate the elements at various points in the use of the article. The releasable bond strengths between these components are designed to have a preferred relationship that assists in the use of the fastening device 41. The releasable bond strengths desired may be provided by several means.

A releasable tab to tab bond 81 is designed to act between the first tab 51 and the second tab 61. The releasable tab to tab bond 81 may be located anywhere on the first tab 51, the second tab 61, or both. As shown in FIG. 3, the releasable tab to tab bond 81 is located on the second tab inner surface 62 and first tab outer surface 53. Alternatively, at least a portion of the releasable tab to tab bond 81 may be on the first tab outer surface 53, the second tab fastening element 64, or both. The releasable tab to tab bond 81 may be created by adhesives, cohesives, hook materials, loop materials, snaps, buttons, tabs, slots, magnets and combinations thereof as are know to those skilled in the art. The tab to tab bond 81 may also be a mechanical bond such as bonds created by ultrasonic, pressure, or thermal energy. The releasable tab to tab bond 81 may have any shape such as a circle, square, rectangle, or triangle.

The releasable tab to tab bond 81 has a release load which is the load required to release the releasable tab to tab bond 81, allowing the first tab 51 and the second tab 61 to separate. The release load may also be referred to as bond strength. The separation is designed to occur between the first tab outer surface 53 and the second tab inner surface 61. Generally, the release load should be measured relative to how the fastening device 41 will normally be used and released. This would suggest that the release load should be measured as a peel load at any angle out of the plane of the article inner surface 271. The peel load should be measured only once on the first release of the tab to tab bond release load since the releasable tab to tab bond 81 may be designed to have the strongest release load during the first release.

A releasable storage fastening bond 82 is designed to act between the stored landing zone 45 and the first fastening member 42. The releasable storage fastening bond 82 may act between the stored landing zone 45 and the first tab fastening element 54 as shown in FIG. 3. The releasable storage fastening bond 82 may also be created between the stored landing zone 45 and the first tab inner surface 52, first tab fastening element 54, second tab inner surface 62, second tab fastening element 64, or a combination thereof. The releasable storage fastening bond 82 may be created by adhesives, cohesives, hook materials, loop materials, snaps, buttons, tabs, slots, magnets and combinations thereof. The releasable storage fastening bond 82 may also be a mechanical bond such as bonds created by ultrasonic, pressure, or thermal energy. The releasable storage fastening bond 82 may have any shape such as a circle, square, rectangle, or triangle.

The releasable storage fastening bond 82 includes a release load which is the load required to release the first fastening member 42 from the stored landing zone 45. Preferably, the releasable storage fastening bond release load is greater than about 50 grams force (gf). A releasable storage fastening bond release load greater than about 50 gf is designed to help maintain the first fastening member 42 in position during manufacturing, packaging, and prior to use by the consumer. Generally, the releasable storage fastening bond release load should be less than the releasable tab to tab bond release load. Thus, when the first fastening member 42 is lifted from the storage landing zone 45, the first tab 51 and second tab 61 may be lifted together with the releasable tab to tab bond 81 intact. Releasably bonding the first tab 51 and the second tab 61 together such that they remain connected at this point in the article application process is designed to improve the ease of use of the fastening device 41 in general and specifically the use of the first tab 51.

To assist the user's gripping of the first fastening member 42 during the fastening process, the first fastening member 42 may comprise a gripping means 72 as shown in FIG. 1, and FIG. 3. The gripping means 72 may be joined anywhere on the first fastening member 42. Preferably, the gripping means 72 may be joined to the second tab 61. The gripping means 72 may include any means known in the art. Suitable examples include a small extension of easily liftable material not bonded to the stored landing zone 45. Another suitable example includes an adhesive or tacky material on the second tab outer surface 63. Any adhesive or tacky material known in the art may be acceptable.

Figure 4:
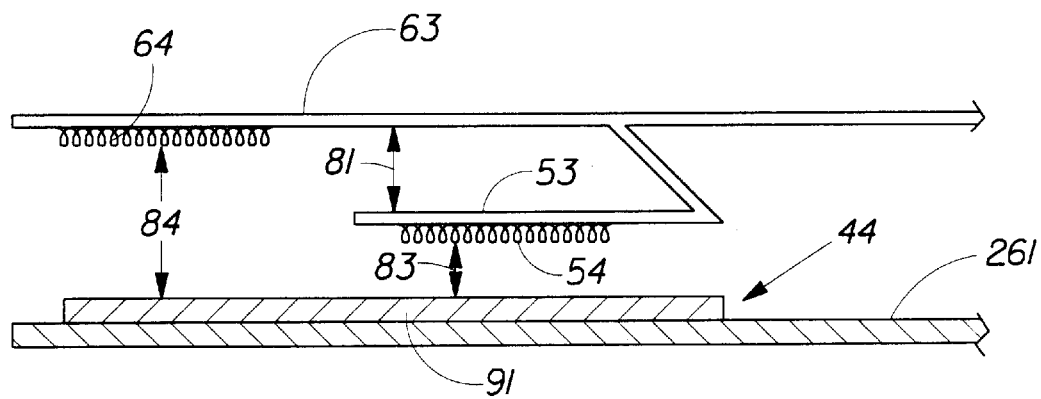
FIG. 4 is an expanded and exploded apart side view of one embodiment of the fastening device and the bonds when fastened.

As shown in FIG. 1, the fastening device may include a second fastening member 44. The second fastening member 44 is designed to be joined to the second waist region 38. As shown in FIG. 4, the second fastening member 44 is designed to be located on the article outer surface 261 and may include at least one attachment landing zone 91. Embodiments are contemplated wherein the second fastening member 44 and the attachment landing zone 91 are equivalent and functionally indistinguishable. In one embodiment, the second fastening member 44 may be the backsheet 26. The attachment landing zone 91 is the location or locations, on the second fastening member 44 where the first tab fastening element 54 and second tab fastening element 64 attach. The first tab fastening element 54 and second tab fastening element 64 are configured to provide an operably secure, fastening engagement with the attachment landing zone 91. The second fastening member 44 is designed to be the preferred attachment point for the first fastening member 42 to join at least a portion of the first waist region 36 with at least a portion of the second waist region 38 as shown in FIGS. 2, 5, 6A and 6B. The attachment landing zone 91 may include any fastening element known in the art including, plastics, adhesives, cohesives, hook materials, loop materials, snaps, buttons, tabs, slots, magnets and combinations thereof as are known to those skilled in the art. The attachment landing zone 91 designed to be fastened with the first tab fastening element 54, may comprise a different loop material than the attachment landing zone 91 designed to be fastened with the second tab fastening element 64. The attachment landing zone 91 may have any shape such as a circle, square, rectangle or triangle. The attachment landing zone 91 may also be located in two or more locations on the second waist region.

The first tab 51 and second fastening member 44 are designed to be fastened together by the user. Preferably, the first tab fastening element 54 and the attachment landing zone 91 are fastened as shown in FIG. 4 with a releasable bond. FIG. 4 shows the first fastening member 42 in an exploded side view when in a deployed position relative to the second fastening member 44. The exaggerated separation of the elements allows a visual representation of the various components in a fastened orientation. The releasable bonds are designed to be strong enough to function as desired, but weak enough so that a user may break them and separate the elements at various points in the use of the article. The releasable bonds have a release load between these components designed to have a preferred relationship that assists in the use of the fastening device 41. When the first tab fastening element 54 and the attachment landing zone 91 are fastened, a first releasable fastening bond 83 between the first tab fastening element 54 and the attachment landing zone 91 is created as shown in FIG. 4. The first releasable fastening bond 83 may be created by adhesives, cohesives, hook materials, loop materials, snaps, buttons, tabs, slots, magnets and combinations thereof. The first releasable fastening bond 83 may also be a mechanical bond such as bonds created by ultrasonic, pressure, or thermal energy. The first releasable fastening bond 83 may have any shape such as a circle, square, rectangle, or triangle.

The first releasable fastening bond 83 has a release load which is the load required to release the first releasable fastening bond 83, allowing the first tab fastening element 54 and attachment landing zone 91 to separate. Preferably, the first releasable fastening bond release load is greater than the releasable tab to tab bond release load. The stronger first releasable fastening bond release load is designed to allow the first tab 51 and second tab 61 to be separated without disengaging the first tab 51 from the attachment landing zone 91.

After the first tab 51 and the attachment landing zone 91 are fastened, the user may fasten the second tab fastening element 64 and the attachment landing zone 91 creating a second releasable fastening bond 84. The second releasable fastening bond 84 may be created from adhesives, cohesives, hook materials, loop materials, snaps, buttons, tabs, slots, magnets and combinations thereof. The second releasable fastening bond 84 may have any shape such as a circle, square, rectangle or triangle.

The second releasable fastening bond 84 has a release load which is the load required to release the second releasable fastening bond 84, allowing the second tab fastening element 54 and attachment landing zone 91 to separate. In one embodiment, the second releasable fastening bond release load is greater than or equal to the first releasable fastening bond release load. A stronger second releasable fastening bond release load may help maintain the article 20 in the desired position on the wearer during use. The first tab fastening element 54 and the attachment landing zone 91 may also remain attached after the second tab fastening element 64 and the attachment landing zone 91 are fastened. Alternatively, the first tab fastening element 54 and the attachment landing zone 91 may release and disengage at any time after the second tab fastening element 64 and the attachment landing zone 91 are fastened.

In one example of the present invention a suitable bond relationship may be created using KN1543 release tape, supplied by 3M Inc., of St Paul, Minn. as the first tab 51 and KN1770 fastening tape, supplied by 3M of St. Paul, Minn. as the second tab 61. The release surface of KN1543 releasably bonds to the adhesive surface of KN1770 to form the releasable tab to tab bond 81. Hook material 960E supplied by Aplix U.S., of Charlotte, N.C. may be used as the hook material for the first tab fastening element 54 and second tab fastening element 64. 3M loop material XPL00008 may be used as the second fastening member 44. Aplix hook material 960E and the adhesive surface of KN1543 releasably bond to the stored landing zone 45 to form the releasable storage fastening bond 82.

During the application of the product about the wearer, the first fastening member 42 may be separated from the stored landing zone 45, as shown on the right side of FIG. 1 and in FIG. 2. The user may then choose any of several means of applying the article 20 to a wearer. One means for applying the article 20 may include placing the article 20, unfastened in the desired wearer waist location and securing the article 20 in place with the second tab fastening element 64 without releasing the releasable tab to tab bond 81. Alternatively, the user may place the article 20 in approximately the desired wearer waist location and attach the first fastening element 54 to the attachment landing zone 91. The user may then refine the article 20 position as desired and cinch the article 20 securely in the desired wearer waist location by fastening the second tab fastening element 64 to the attachment landing zone 91. The desired wearer waist location is generally within about 25 centimeters above or below the wearer's hips and about their waist. More preferably, the desired wearer waist location is generally within about 10 centimeters above or below the wearer's hips and about their waist. Also alternatively, the user may attach the first fastening element 54 to the attachment landing zone 91 about the wearer's legs creating one or more leg openings 10 as shown in FIG. 2. The user may then use the article 20 as a typical pull-up. Once the article 20 is in the desired location about the wearer's waist, it may then be secured in place by fastening the second tab fastening element 64 to the attachment landing zone 91.

Figure 5:
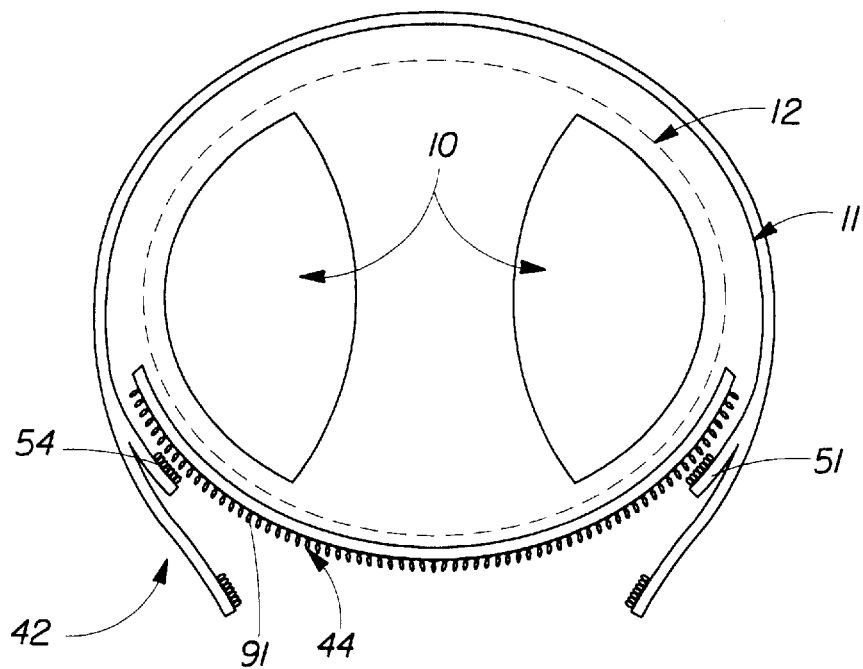
FIG. 5 is a top cross-sectional view of one embodiment of the absorbent article with the first tab fastened forming a first article circumference.

The article may also be delivered to the user with at least one first tab fastening element 54 prefastened to the attachment landing zone 91 forming at least one leg opening 10 as shown in FIG. 5. The first tab fastening element 54 may be releasably prefastened to the attachment landing zone 91 with, adhesives, cohesives, hook materials, loop materials, snaps, buttons, tabs, slots, magnets and combinations thereof as are know to those skilled in the art. The first tab fastening element 54 may also be a mechanical bond such as bonds created by ultrasonic, pressure, or thermal energy. The user may then use the article as a pull-up. Alternatively, the user may disconnect the prefastened first tab fastening element 54 and attachment landing zone 91 and use the article 20 as described above. At least one first tab fastening element 54 may also be permanently prefastened to the second fastening member and/or the attachment landing zone 91 with ultrasonics, bonds, heat bonding, adhesives, cohesives, hook materials, loop materials, snaps, buttons, tabs, slots, magnets and combinations thereof as are know to those skilled in the art. Embodiments are contemplated wherein only one first tab fastening element 54 is prefastened and the article is used as a pull-up on one of the wearer's legs and fastened and cinched during the application process on the other leg.

As shown in FIG. 5, when the at least one first tab fastening element 54 and the attachment landing zone 91 are fastened, an article waist 35 having a first waist hoop dimension 11 is formed. The first waist hoop 11 has a first waist hoop tension. In general, the first waist hoop dimension may or may not correspond with the waist dimension of the wearer herein defined as a target waist hoop dimension 12 shown in FIG. 5 and FIG. 6A.

Figure 6A:
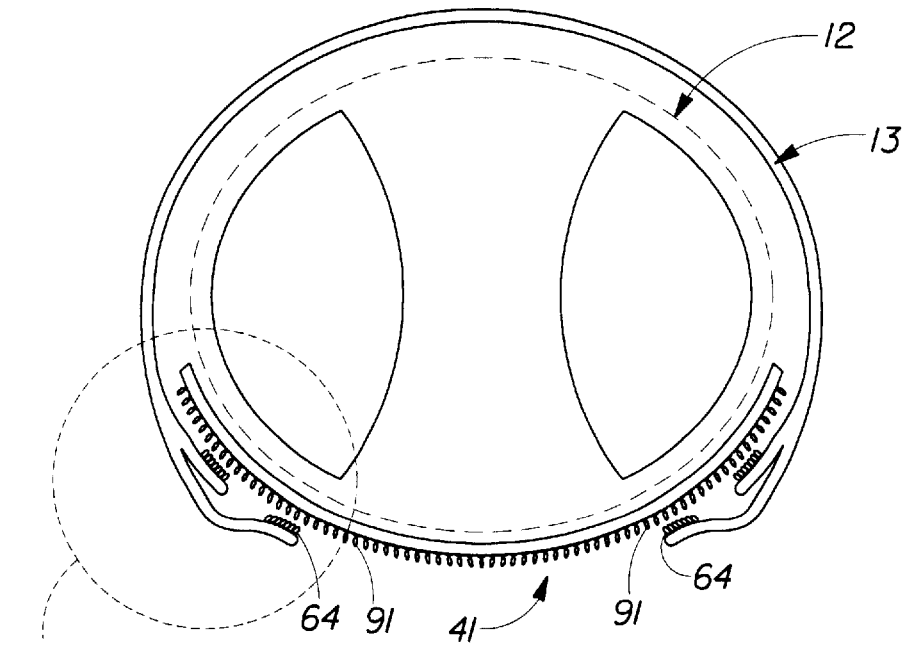
FIG. 6A is a top cross-sectional view of one embodiment of the absorbent article with the second tab fastened forming a second article circumference.

As shown in FIG. 6a, when the at least one second tab fastening element 64 and the attachment landing zone 91 are fastened, an article waist 35 having a second waist hoop dimension 13 is formed. The second waist hoop 13 has a second waist hoop tension. In general, the second waist hoop dimension corresponds closely with the waist dimension of the wearer herein defined as a target waist hoop dimension 12 shown in FIG. 5 and FIG. 6A.

The fastening system works in conjunction with other elements of the article 20 to create an article waist 35 which can be assembled in different configurations. The article may have a first waist hoop dimension 11 and a second waist hoop dimension 13 that are the same, or different. The article 20 may also have a first waist hoop tension and a second waist hoop tension that are the same, or different. Preferably, the second waist hoop 13 is smaller than the first waist hoop 11. Also preferably, the second waist tension is greater than the first waist tension. This allows improved the ease of application of the product while assuring the product reliably remains in place during wearing.

The first waist hoop tension level is lower than the second waist hoop tension level. This allows the product to be pulled up easily while the product is configured at the first waist hoop tension level, yet reliably remain in place during wearing at the second waist hoop tension level.

The first waist hoop tension level may be about 0 grams force (gf) or greater at the first waist hoop dimension 11. Preferably, the ratio of the first waist hoop tension to the second waist hoop tension is from about 0 to about 0.9

In embodiments in which the first waist hoop dimension 11 and second waist hoop dimension 13 are different, it is preferred to not have too great a difference between the first waist hoop dimension 11 and second waist hoop dimension 13. If the difference is too great, an undue amount of material will have to be gathered by the user in switching between the the first waist hoop dimension 11 and second waist hoop dimension 13. This can inhibit ease of use. Preferably, the waist hoop dimension ratio between the second waist hoop dimension 13 and the first waist hoop dimension 11 is from about 0.55 to about 0.95.

Figure 6B:
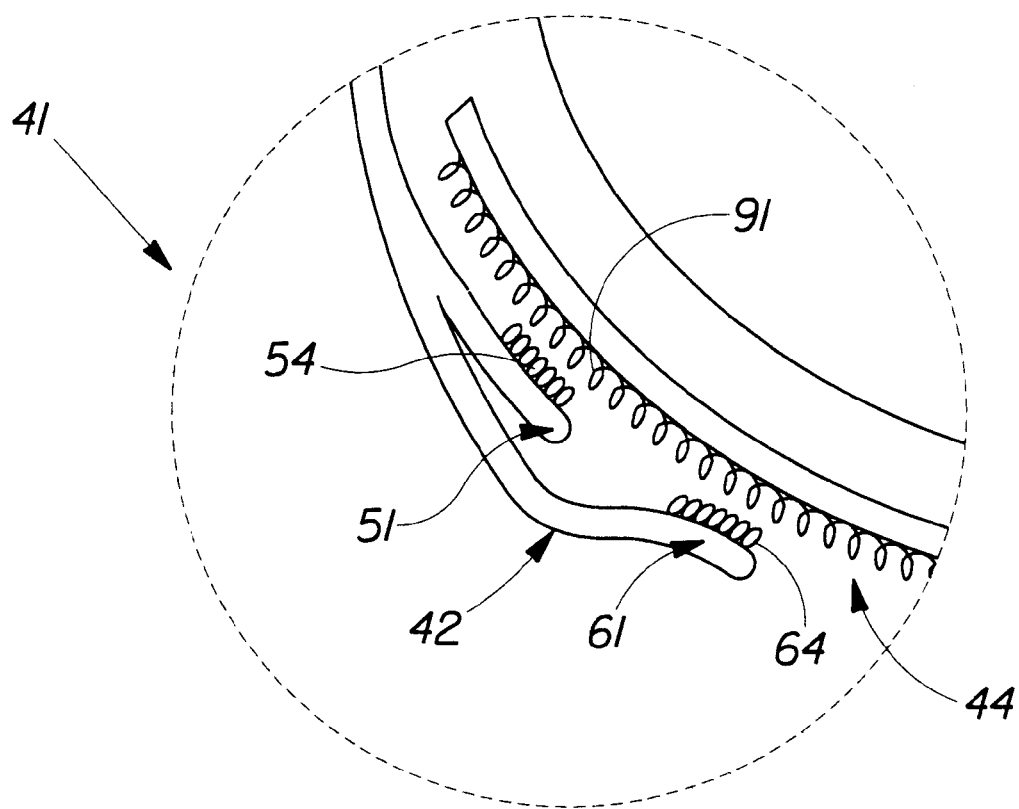
FIG. 6B is a side view of one embodiment of article fastening device.

FIG. 6B is a close-up side view of one embodiment of the fastening device 41 engaged. The first fastening member 42 and second fastening member are shown relative to one another for engagement. The first tab 51 has the first tab fastening element 54 slightly exploded and relative to the attachment landing zone 91. The second tab 61 and second tab fastening element 64 are also slightly exploded and relative to the attachment landing zone 91.

The first waist region 36 and second waist region 38 may be more than about 10% elastomeric or extensible under a load of about 20 grams force/centimeter or greater. The elasticity or extensibility is designed to assist the pull-up and/or cinch of the absorbent article.

The first waist region 36 and second waist region 38 are used herein to differentiate the portions of the article being attached. For simplicity the first fastening member 42 is herein described as being joined to the first waist region 36 and the second fastening member 44 is herein described as being joined to the second waist region 38. However, the two regions and two fastening members are generally interchangeable, e.g. the second fastening member could be located on the first waist region in alternate embodiments. The present invention may be readily adapted to many product forms and is intended to cover all such changes and modifications that are within the scope of this invention in the following claims.

What is claimed is:

1. An absorbent article having a first waist region, a second waist region and a crotch region interconnecting the first waist region and second waist region, an article inner surface and an article outer surface, the absorbent article comprising:
   a topsheet;
   a backsheet;
   a fastening device for joining at least a portion of the first waist region with at least a portion of the second waist region, the fastening device including at least one first fastening member, and at least one second fastening member;
      the first fastening member is joined to the first waist region, the first fastening member includes,
         at least one first tab, the first tab including a first tab inner surface, a first tab outer surface, and a first tab fastening element on to the first tab inner surface,
         at least one second tab, the second tab including a second tab inner surface, a second tab outer surface, and a second tab fastening element on the second tab inner surface,
         a releasable tab to tab bond between the first tab outer surface and the second tab inner surface, the releasable tab to tab bond having a release load,
      at least one second fastening member joined to the second waist region on the article outer surface;
   each first tab fastening element and second tab fastening element are configured to provide an operably secure, fastening engagement with the second fastening member, wherein the fastening device includes at least one stored landing zone on the article inner surface, a releasable storage fastening bond between the stored landing zone and the first fastening member, the releasable storage fastening bond having a release load that is less than the releasable tab to tab bond release load.

2. The absorbent article of claim 1, wherein the releasable storage fastening bond is selected from the group comprising adhesives, cohesives, hook materials, loop materials, and combinations thereof.

3. An absorbent article having a first waist region, a second waist region and a crotch region interconnecting the first waist region and second waist region, an article inner surface and an article outer surface, the absorbent article comprising:
   a topsheet;
   a backsheet;
   a fastening device for joining at least a portion of the first waist region with at least a portion of the second waist region, the fastening device including at least one first fastening member, and at least one second fastening member;
      the first fastening member is joined to the first waist region, the first fastening member includes,
         at least one first tab, the first tab including a first tab inner surface, a first tab outer surface, and a first tab fastening element on to the first tab inner surface,
         at least one second tab, the second tab including a second tab inner surface, a second tab outer surface, and a second tab fastening element on the second tab inner surface,
         a releasable tab to tab bond between the first tab outer surface and the second tab inner surface, the releasable tab to tab bond having a release load,
      at least one second fastening member joined to the second waist region on the article outer surface;
   each first tab fastening element and second tab fastening element are configured to provide an operably secure, fastening engagement with the second fastening member, wherein a first releasable fastening bond between the first tab fastening element and the second fastening member has a release load that is greater than the releasable tab to tab bond release load.

4. The absorbent article of claim 3, wherein a second releasable fastening bond between the second tab fastening element and the second fastening member has a release load that is greater than or equal to the first releasable fastening bond release load.

5. The article of claim 4, wherein the first tab fastening element is a hook material, the second tab fastening element is a second hook material, and the second fastening member includes at least two attachment landing zones of different loop material.

6. The article of claim 4, wherein the first tab fastening element and attachment landing zone are prefastened.

7. The absorbent article of claim 3, wherein the releasable combined tab fastening bond is selected from the group comprising adhesives, cohesives, hook materials, loop materials, and combinations thereof.

8. The absorbent article of claim 3, wherein the first releasable fastening bond is selected from the group comprising adhesives, cohesives, hook materials, loop materials, and combinations thereof.

9. The absorbent article of claim 3, wherein the second releasable fastening bond is selected from the group comprising adhesives, cohesives, hook materials, loop materials, and combinations thereof.

10. The absorbent article of claim 3, wherein the first tab has a first tab length and the second tab has a second tab length, and the second tab length is greater than the first tab length.

11. The absorbent article of claim 10, wherein the second tab length is equal to the first tab length.

12. An absorbent article having a first waist region, a second waist region and a crotch region interconnecting the first waist region and second waist region, an article inner surface and an article outer surface, the absorbent article comprising:
   a topsheet;
   a backsheet;
   a fastening device for joining at least a portion of the first waist region with at least a portion of the second waist region, the fastening device including at least one first fastening member, and at least one second fastening member;
   the first fastening member is joined to the first waist region, the first fastening member includes,
      at least one first tab, the first tab including a first tab inner surface, a first tab outer surface, and a first tab fastening element on to the first tab inner surface,
      at least one second tab, the second tab including a second tab inner surface, a second tab outer surface, and a second tab fastening element on the second tab inner surface,
      a releasable tab to tab bond between the first tab outer surface and the second tab inner surface, the releasable tab to tab bond having a release load,
   at least one second fastening member joined to the second waist region on the article outer surface;
   each first tab fastening element and second tab fastening element are configured to provide an operably secure, fastening engagement with the second fastening member, wherein the first fastening member includes a gripping means.

13. An absorbent article having a first waist region, a second waist region and a crotch region interconnecting the first waist region and second waist region, an article inner surface and an article outer surface, the absorbent article comprising:
   a topsheet;
   a backsheet;
   a fastening device for joining at least a portion of the first waist region with at least a portion of the second waist region, the fastening device including at least one first fastening member, and at least one second fastening member;
   the first fastening member is joined to the first waist region, the first fastening member includes,
      at least one first tab, the first tab including a first tab inner surface, a first tab outer surface, and a first tab fastening element on the first tab inner surface,
      at least one second tab, the second tab including a second tab inner surface, a second tab outer surface, and a second tab fastening element on the second tab inner surface,
   the second fastening member is joined to the second waist region on the article outer surface and includes at least one attachment landing zone; wherein
      when the at least one first tab fastening element and the attachment landing zone are fastened, a first waist hoop is formed,
      wherein the article is positioned at a target article location and the at least one second tab fastening element is fastened to the attachment landing zone, a second waist hoop is formed, a ratio of the second waist hoop to the first waist hoop is from about 0.55 to about 0.95, wherein the article is a diaper, or pull-up.

14. An absorbent article having a first waist region, a second waist region and a crotch region interconnecting the first waist region and second waist region, an article inner surface and an article outer surface, the absorbent article comprising:
   a topsheet;
   a backsheet;
   the first waist region and the second waist region are prefastened forming at least one leg opening;
   a fastening device for joining at least a portion of the first waist region with at least a portion of the second waist region, the fastening device including at least one first fastening member, and at least one second fastening member;
   the first fastening member is joined to the first waist region, the first fastening member includes,
      at least one first tab, the first tab including a first tab inner surface, a first tab outer surface, and a first tab fastening element on the first tab inner surface,
      at least one stored landing zone on the article,
         a releasable storage fastening bond between the stored landing zone and the first fastening member, the releasable storage fastening bond having a release load,
   the second fastening member is joined to the second waist region on the article outer surface;
   each first tab fastening element is configured to provide an operably secure, fastening engagement with the second fastening member, wherein the first tab and a portion of the second fastening member are permanently prefastened.

15. An absorbent article having a first waist region, a second waist region and a crotch region interconnecting the first waist region and second waist region, an article inner surface and an article outer surface, the absorbent article comprising:
   a topsheet;
   a backsheet;
   the first waist region and the second waist region are prefastened forming at least one leg opening;
   a fastening device for joining at least a portion of the first waist region with at least a portion of the second waist region, the fastening device including at least one first fastening member, and at least one second fastening member;
   the first fastening member is joined to the first waist region, the first fastening member includes,
      at least one first tab, the first tab including a first tab inner surface, a first tab outer surface, and a first tab fastening element on the first tab inner surface, at least one stored landing zone on the article,
- a releasable storage fastening bond between the stored landing zone and the first fastening member, the releasable storage fastening bond having a release load, the second fastening member is joined to the second waist region on the article outer surface;

each first tab fastening element is configured to provide an operably secure, fastening engagement with the second fastening member, wherein the first fastening member includes at least one second tab, the second tab including a second tab inner surface, a second tab outer surface, and a second tab fastening member on the second tab inner surface.

16. The article of claim 15, wherein the second fastening member includes at least two attachment landing zones of different material.

17. An absorbent article having a first waist region, a second waist region and a crotch region interconnecting the first waist region and second waist region, an article inner surface and an article outer surface, the absorbent article comprising:

a topsheet;

a backsheet;

the first waist region and the second waist region are prefastened forming at least one leg opening;

a fastening device for joining at least a portion of the first waist region with at least a portion of the second waist region, the fastening device including at least one first fastening member, and at least one second fastening member;

the first fastening member is joined to the first waist region, the first fastening member includes,
- at least one first tab, the first tab including a first tab inner surface, a first tab outer surface, and a first tab fastening element on the first tab inner surface,
- at least one stored landing zone on the article,
- a releasable storage fastening bond between the stored landing zone and the first fastening member, the releasable storage fastening bond having a release load, the second fastening member is joined to the second waist region on the article outer surface;

each first tab fastening element is configured to provide an operably secure, fastening engagement with the second fastening member, wherein the first and second waist regions are more than about 10% elastomeric or extensible under a load of about 80 grams force/centimeter or greater.

* * * * *